United States Patent [19]  
Lee et al.

[11] 4,079,075  
[45] Mar. 14, 1978

[54] PRIMARY ALKYL ESTERS AS MEDIUMS FOR OXIDATIONS BY PHASE-TRANSFER CATALYZED HYPOHALITES

[75] Inventors: George A. Lee, Wayland; Harold H. Freedman, Newton Center, both of Mass.

[73] Assignee: The Dow Chemical Company, Midland, Mich.

[21] Appl. No.: 782,136

[22] Filed: Mar. 28, 1977

Related U.S. Application Data

[63] Continuation-in-part of Ser. No. 629,337, Nov. 6, 1975, abandoned.

[51] Int. Cl.$^2$ ............... C07C 120/14; C07C 47/54; C07C 45/00; C07C 45/16
[52] U.S. Cl. ............... 260/464; 260/465 R; 260/465 B; 260/465.1; 260/465.2; 260/530 R; 260/586 P; 260/599; 260/600 R
[58] Field of Search .......... 260/464, 465.1, 586 P, 260/600 R, 465 B, 465 R, 599, 530 R, 465.2

[56] References Cited

U.S. PATENT DOCUMENTS

| | | | |
|---|---|---|---|
| 2,375,016 | 5/1945 | Marple et al. | 260/464 X |
| 3,940,429 | 2/1976 | McConaghy Jr. et al. | 260/464 X |
| 3,941,827 | 3/1976 | Johnson | 260/464 X |
| 3,992,432 | 11/1976 | Napier et al. | 260/465.1 X |
| 3,996,259 | 12/1976 | Lee et al. | 260/465.1 X |

FOREIGN PATENT DOCUMENTS

| | | | |
|---|---|---|---|
| 1,227,144 | 4/1971 | United Kingdom | 260/465.1 |
| 1,324,763 | 7/1973 | United Kingdom | 260/465.1 |

OTHER PUBLICATIONS

Lee et al., Tetrahedron Letters, 20 (May, 1976), pp. 1641–1644.

*Primary Examiner*—Joseph Paul Brust  
*Attorney, Agent, or Firm*—G. R. Plotecher; L. W. White

[57] ABSTRACT

The process of oxidizing organic compounds by dissolving the organic compound in a water-immiscible, inert organic solvent and contacting same with an aqueous hypohalite ion in the presence of a catalytic amount of a quaternary onium salt is improved by employing a primary alkyl ester as the organic solvent. For example, cyclohexylmethylamine is oxidized under mild conditions to a high yield of cyclohexylnitrile by dissolving the amine in ethyl acetate and contacting same with aqueous hypochlorite and in the presence of a catalytic amount of tetra-n-butylammonium chloride.

4 Claims, No Drawings

PRIMARY ALKYL ESTERS AS MEDIUMS FOR OXIDATIONS BY PHASE-TRANSFER CATALYZED HYPOHALITES

CROSS-REFERENCE TO RELATED APPLICATION

This application is a continuation-in-part of application Ser. No. 629,337, filed Nov. 6, 1975, now abandoned

BACKGROUND OF THE INVENTION

1. Field of the Invention

This invention relates to a process for oxidizing organic compounds oxidizable by hypohalite ion. In one aspect, this invention relates to such a process wherein the compound to be oxidized is dissolved in a water-immiscible, inert organic solvent and subsequently contacted with an aqueous hypohalite ion in the presence of a catalytic amount of a quaternary onium salt. In another aspect, this invention relates to said process wherein the water-immiscible, inert organic solvent is a primary alkyl ester.

2. Description of the Prior Art

Lee et al., U.S. Pat. No. 3,996,259, is incorporated herein by reference. Disclosed therein is a novel process for oxidizing certain organic compounds which comprises contacting:

(a) a water-immiscible, liquid organic phase comprising the organic compound to be oxidized; with
(b) an aqueous phase containing hypohalite ion; and
(c) a catalytic amount of a quaternary ammonium salt and/or a quaternary phosphonium salt.

The water-immiscible, organic solvents used therein, e.g., methylene chloride, chloroform, and the like, are typical of the known organic solvents in which quaternary onium salts are soluble. The present invention differs from and is an improvement over the invention of U.S. Pat. No. 3,996,259 by the use of a primary alkyl ester as the water-immiscible, organic solvent.

SUMMARY OF THE INVENTION

The process of oxidizing an organic compound selected from the group consisting of amines, amides, aldehydes, primary and secondary alcohols, and organic compounds containing an activated carbon-carbon double bond with aqueous hypohalite ion, the process comprising contacting:

(a) a water-immiscible, liquid organic phase comprising the organic compound and a water-immiscible, organic solvent; with
(b) an aqueous phase containing hypohalite ion; and
(c) a catalytic amount of a quaternary ammonium salt and/or a quaternary phosphonium salt is surprisingly improved by using as the water-immiscible, organic solvent a primary alkyl ester of the formula:

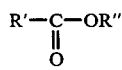

wherein R' is alkyl, aryl or an inertly-substituted alkyl or aryl radical and R" is alkyl or inertly-substituted alkyl from 1 to about 10 carbon atoms. These oxidations are faster and more complete than similar oxidations performed in solvents other than primary alkyl esters.

DETAILED DESCRIPTION OF THE INVENTION

The water-immiscible, inert organic solvent may be any known, suitable primary alkyl ester. Said ester is of the formula:

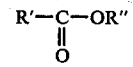

wherein R' is alkyl, aryl or an inertly-substituted alkyl or aryl radical (e.g., aralkyl, alkaryl, cycloalkyl, haloalkyl, haloaryl, etc.) and R" is alkyl or inertly-substituted alkyl of from 1 to about 10 carbon atoms and preferably from 1 to 4 carbon atoms. Inertly-substituted means that the alkyl or aryl moieties bear substituents that do not react with the process reagents or reaction products under process conditions. Members of this known class of compounds include: Ethyl acetate, propionate, butyrate, valerate, caprylate, caprate, etc.; ethyl 3-chloropropionate, ethyl 3-chlorobutyrate, etc; n-propyl acetate, propionate, butyrate, valerate, caprylate, caprate, etc.; 2-bromobutyl acetate, propionate, etc; ethylbenzyl acetate, propylbenzyl acetate, etc.; and the like. Solvents wherein R' is alkyl are preferred with ethyl acetate especially preferred. The esters can be used alone or in combination with one another.

Sufficient ester solvent to dissolve the compound to be oxidized is required. Preferably, the amount of ester used is essentially equal in volume to the amount of aqueous hypohalite used. Practical considerations, such as reaction vessel size, ease of product recovery, etc., are the only limitations upon the maximum amount of ester that can be used.

The following examples are illustrative embodiments of this invention. However, these examples are for illustrative purposes only and should not be construed as limitations upon the invention. Unless otherwise indicated, all parts and percentages are by weight.

SPECIFIC EMBODIMENTS

EXAMPLE 1:

A mixtures of 2-norbornanol (1.1696 g, 0.01044 mole), n-heptylchloride (1.0222 g, employed as an internal standard) and tetra-n-butylammonium bisulfate (o.1834 g, 0.0005 mole) in 25 ml of ethyl acetate was stirred magnetically at ambient conditions (24° C, atmospheric pressure) with 25 ml of 10 percent aqueous sodium hypochlorite. The reaction progress was monitored periodically by vapor phase chromatography and after 78 minutes the mixture contained 35.6% norbornanone and 61.5% 2-norbornanol.

Control A:

The procedure of Example 1 was repeated except that carbon tetrachloride was substituted for ethyl acetate. After 635 minutes of reaction, the mixture contained 58% unreacted starting material (2-norbornanol) and 33% norbornanone.

EXAMPLE 2:

A mixture of cyclohexylmethylamine (1.085 g, 0.0096 mole), 2-chloronaphthalene (1.0125 g, employed as an internal standard), and tetra-n-butylammonium chloride (0.1529 g, 0.0005 mole) in 25 ml of ethyl acetate was magnetically stirred with 50 ml of 10 percent aqueous sodium hypochlorite under ambient conditions (24° C, atmospheric pressure). After 40 minutes of reaction, vapor phase chromatographic analysis indicated 75% of the starting material had been converted to cyclohexylnitrile.

EXAMPLES 3-5 AND CONTROLS B-D:

A series of reactions were conducted under conditions similar to Example 1 and Control A and the results summarized in Table I. The product yield is based on starting materials.

TABLE I

| Ex. & Con. | Solvent | Oxidizable Substrate (mole) | Alkali Metal Hypohalite (mole) | Quaternary Onium Salt (mole) | Reaction Time (min) | Product Yield % |
|---|---|---|---|---|---|---|
| 3 | EtOAc[1] | Cycloheptanol (0.3) | NaOCl (0.4) | Bu$_4$NHSO$_4$[2] (0.012) | 58 | Cycloheptanone (89) |
| B | CH$_2$Cl$_2$ | Cycloheptanol (0.3) | NaOCl (0.4) | Bu$_4$NCl[3] (0.012) | 360 | Cycloheptanone (16) |
| 4 | EtOAc | p-Methoxybenzyl alcohol (0.4) | NaOCl (0.4) | Bu$_4$NHSO$_4$ (0.02) | 28 | p-Methoxybenzylaldehyde (92) |
| C | CH$_2$Cl$_2$ | p-Methoxybenzyl alcohol (0.4) | NaOCl (0.4) | Bu$_4$NHSO$_4$ (0.02) | 75 | p-Methoxybenzylaldehyde (79) |
| 5 | EtOAc | 1-Octylamine (0.1) | NaOCl (0.8) | Bu$_4$NHSO$_4$ (.005) | 35 | 1-Heptylcyanide (60) |
| D | CH$_2$Cl$_2$ | 1-Octylamine (0.1) | NaOCl (0.8) | Bu$_4$NHSO$_4$ (.005) | 85 | 1-Heptylcyanide (58) |

[1]Ethyl Acetate
[2]Tetra-n-butylammonium bisulfate
[3]Tetra-n-butylammonium chloride

CONTROL E

An organic phase of benzaldehyde (1.0771 g, 0.01 mole), naphthalene (1.0511 g, employed as an internal gas chromatographic standard) and tetra-n-butylammonium bisulfate (0.1754 g, 5.17 × 10$^{-4}$ mole) were dissolved in methylene chloride (25 ml) and stirred at room temperature ($\simeq$ 23° C) with 10 percent aqueous sodium hypochlorite (25 ml, 2.993 g, 0.04 mole) for 2 hours and 33 minutes. Gas chromatographic analysis of the organic phase indicated that about 3.8 weight percent of the benzaldehyde was consumed.

EXAMPLE 6

The procedure of Control E was repeated except that ethyl acetate was substituted for methylene chloride. After 2 hours and 34 minutes, gas chromatographic analysis indicated that about 56.8 weight percent of benzaldehyde was consumed. Acidification of the aqueous phase with concentrated hydrochloric acid caused benzoic acid to precipitate. The white precipitate was collected by filtration, dried and weighed (0.6784 g, 56 weight percent of initial benzaldehyde, melting point 120.5°-121.5° C).

The above control and example data clearly demonstrates the profound and unexpected effect of ethyl acetate on the phase-transfer catalyzed hypochlorite oxidations of these various organic compounds.

That which is claimed is:

1. In the process of oxidizing an organic compound selected from the group consisting of amines, amides, aldehydes, primary and secondary alcohols, and organic compounds containing an activated carbon-carbon double bond with aqueous hypohalite ion, the process comprising contacting:
    (a) a water-immiscible, liquid organic phase comprising the organic compound and a water-immiscible, organic solvent; with
    (b) an aqueous phase containing hypohalite ion; and
    (c) a catalytic amount of a quaternary ammonium salt and/or a quaternary phosphonium salt,
the improvement wherein: The water-immiscible, organic solvent is a primary alkyl ester of the formula:

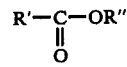

wherein R' is alkyl, aryl or an inertly-substituted alkyl or aryl radical and R" is alkyl or inertly-substituted alkyl from 1 to about 10 carbon atoms.

2. The process of claim 1 wherein R' is alkyl.
3. The process of claim 1 wherein R" is an alkyl of from 1 to 4 carbon atoms.
4. The process of claim 1 wherein the primary alkyl ester is ethyl acetate.

* * * * *